United States Patent [19] [11] 4,127,902
Homsy [45] Dec. 5, 1978

[54] STRUCTURE SUITABLE FOR IN VIVO IMPLANTATION

[76] Inventor: Charles A. Homsy, 11526 Raintree Cir., Houston, Tex. 77024

[21] Appl. No.: 887,512

[22] Filed: Mar. 17, 1978

Related U.S. Application Data

[60] Continuation of Ser. No. 694,054, Jun. 7, 1976, abandoned, which is a division of Ser. No. 489,453, Jul. 17, 1974, Pat. No. 3,971,670.

[51] Int. Cl.² .............................................. A61F 1/24
[52] U.S. Cl. ................................................ 3/1; 3/1.9; 128/92 C; 128/92 G; 128/334 R; 128/DIG. 14
[58] Field of Search ....................... 3/1, 1.4, 1.9–1.911; 128/334 R, 334 C, 335, DIG. 14, DIG. 21, 92 C, 92 G

[56] References Cited

U.S. PATENT DOCUMENTS

| | | | |
|---|---|---|---|
| 3,176,316 | 4/1965 | Bodell | 3/1 |
| 3,463,158 | 8/1969 | Schmitt et al. | 3/1 X |
| 3,479,670 | 11/1969 | Medell | 3/1.4 |
| 3,593,342 | 7/1971 | Niebauer et al. | 3/1.91 |
| 3,744,061 | 7/1973 | Frost | 128/92 CA X |
| 3,797,047 | 3/1974 | Pillet | 3/1 |
| 3,805,300 | 4/1974 | Tascon-Alonso et al. | 3/1 |
| 3,867,728 | 2/1975 | Stubstad et al. | 3/1.91 |
| 3,879,767 | 4/1975 | Stubstad | 3/1.91 |

OTHER PUBLICATIONS

"Porous Implant System for Prosthesis Stabilization" by C. A. Homsy et al., Reprint from Clinical Orthopaedics, No. 89, Nov.–Dec. 1972, pp. 220–235.

Primary Examiner—Ronald L. Frinks
Attorney, Agent, or Firm—Vinson & Elkins

[57] ABSTRACT

A structure suitable for in vivo implantation as a tension member to substitute for tension members such as ligaments and tendons. The structure includes an elongate member which is a biocompatible film, a biocompatible fabric which has a weave having substantially no permanent yield in one direction after said film is formed thereon and a biocompatible porous material which promotes the ingrowth of living tissue and such material is either bonded to the exterior of the elongate member or is contained within and exposed to the exterior. Also disclosed is a structure having a fabric with a film formed thereon and porous ingrowth material bonded to one or both sides thereof to form a patch for in vivo implantation. The film used on the patch may be porous or solid depending on whether the patch is to be permeable to body fluids. The method of making such implantable structures includes the steps of heat forming the plastic film on the fabric folding and forming the combined fabric and film into an elongate structure, bonding the growth material thereto and also inserting heated probes to form apertures in the structure without weakening the fibers of the fabric.

23 Claims, 18 Drawing Figures

U.S. Patent Dec. 5, 1978 Sheet 1 of 5 4,127,902
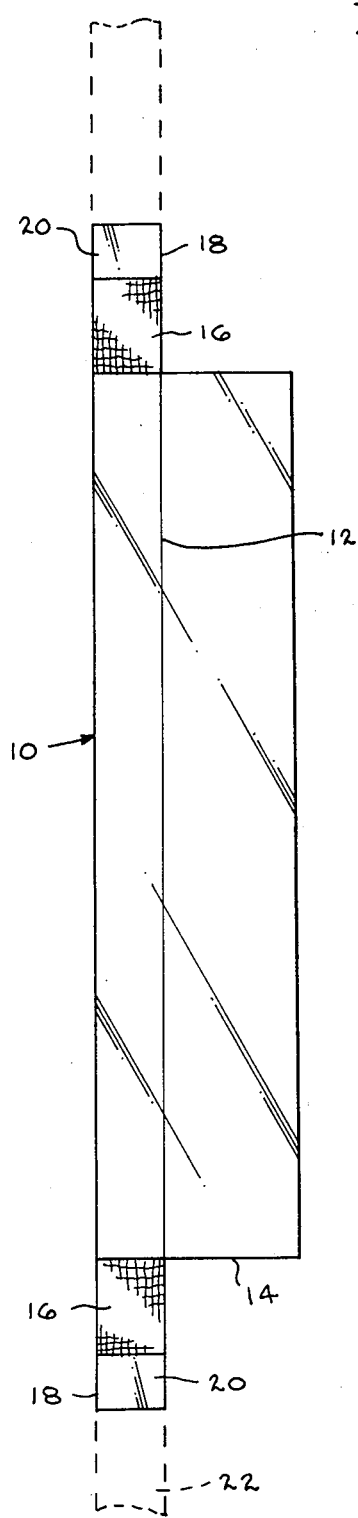
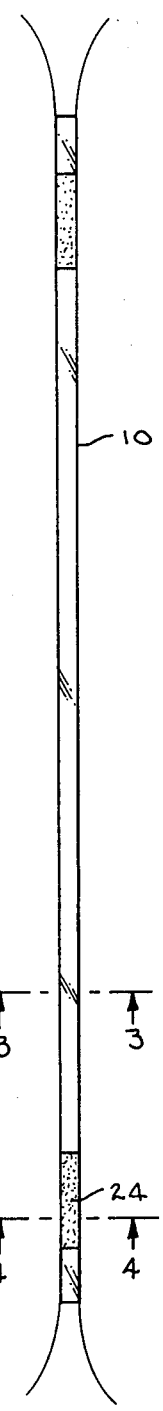
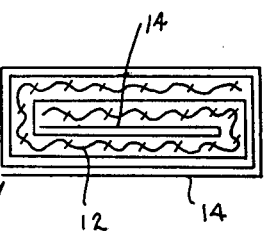
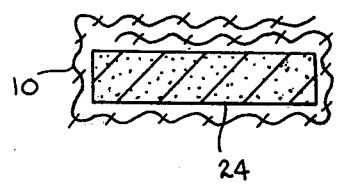
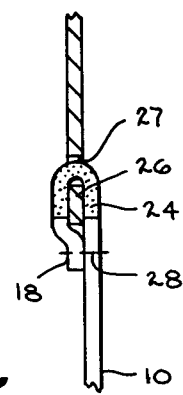

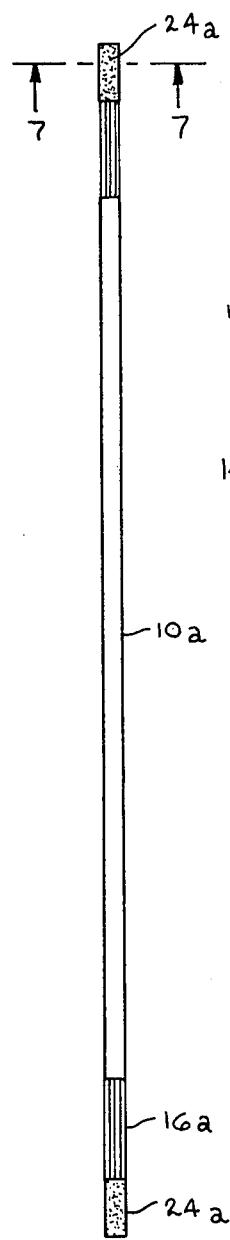
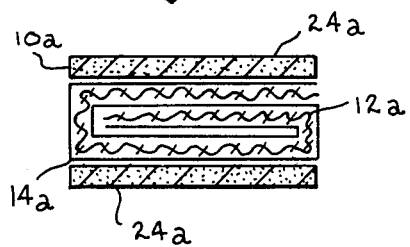
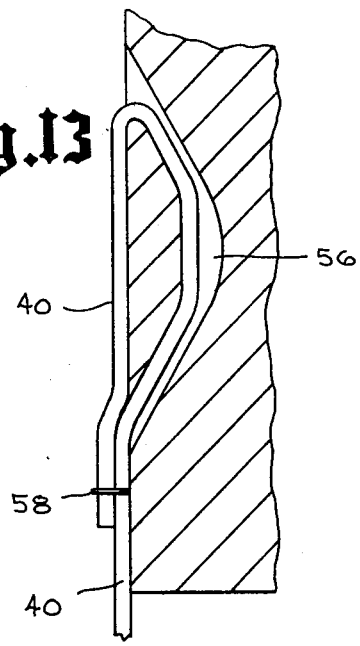
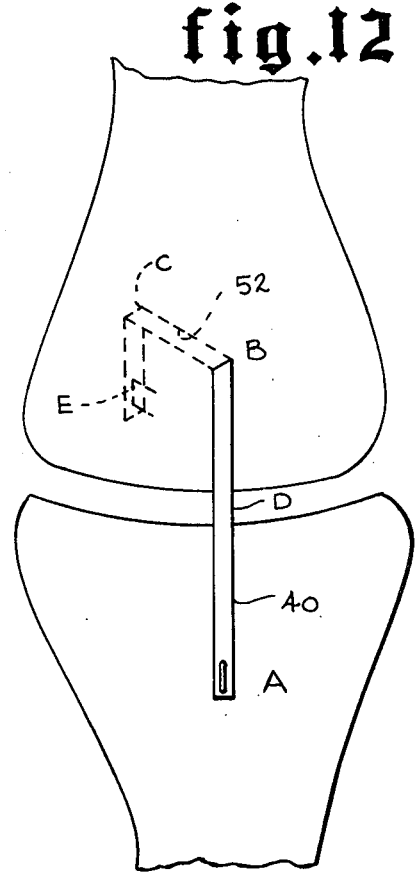
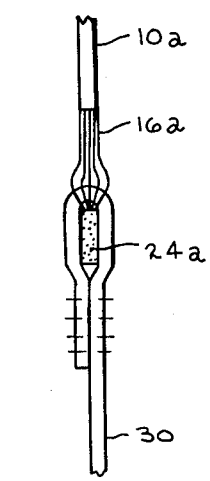

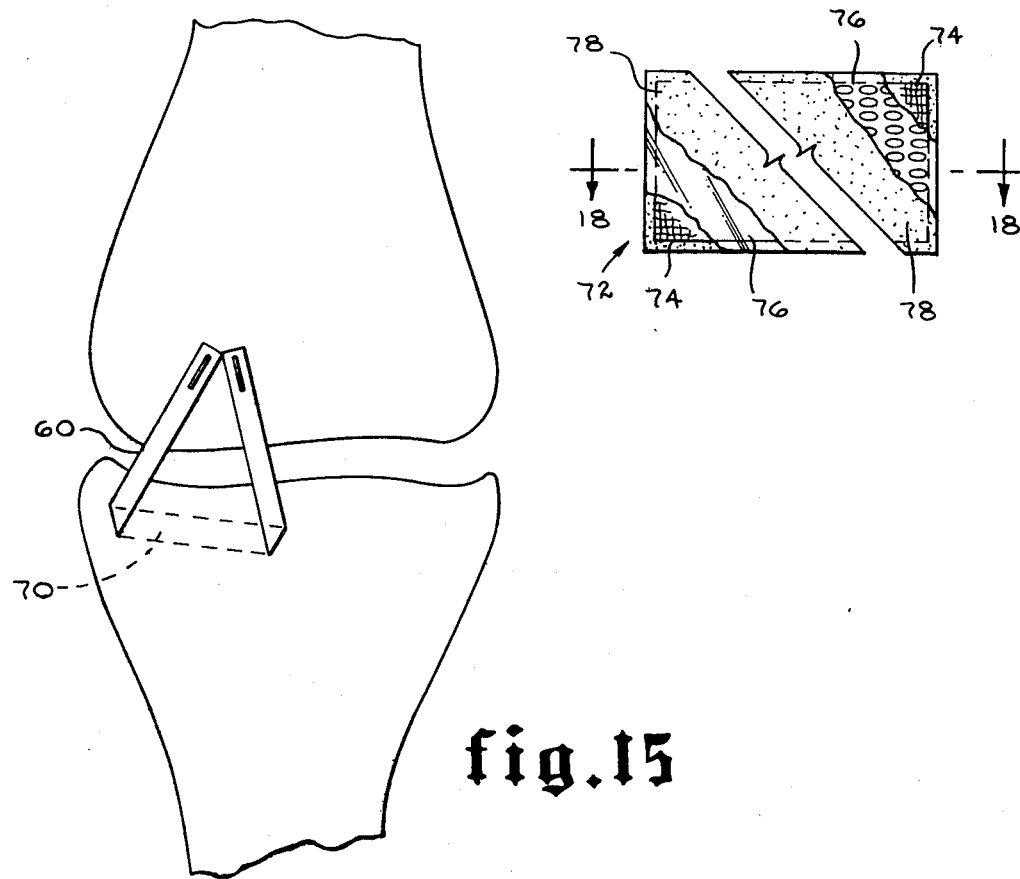
fig.17
fig.15
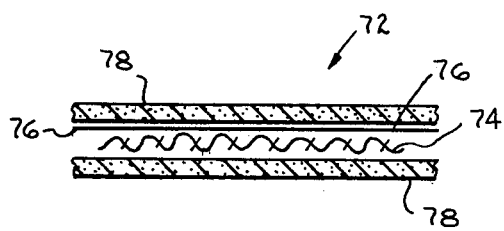
fig.18
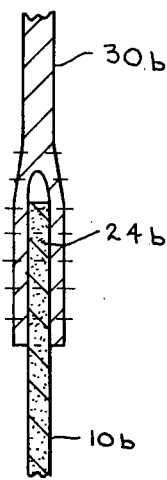
fig.16

STRUCTURE SUITABLE FOR IN VIVO IMPLANTATION

CROSS REFERENCE TO OTHER APPLICATION

The present application is a continuation application of my prior copending application Ser. No. 694,054, filed June 7, 1976 and now abandoned, which was a divisional application of application Ser. No. 489,453, filed July 17, 1974, now U.S. Pat. No. 3,971,670.

BACKGROUND OF THE INVENTION

Many persons suffer from damage to their tendons and ligaments which is beyond surgical repair. This may result in an inconvenience or severe functional disability. Attempts have been made to provide transplants for irreparably damage tendons but to date they have not been entirely successful as the adjacent tissue does not form a tunnel in which the transplant tendon may slide but rather attaches thereto to limit the available movement of the tendon. Also considerable difficulty has been encountered both with transplant and substitute tendons and ligaments in securing them to existing tendons, bone and muscle tissue.

SUMMARY

The present invention relates to a structure suitable for in vivo implantation as tension member.

An object of the present invention is to provide an improved structure for in vivo implantation as a substitute tension member.

Another object is to provide an improved structure for in vivo implantation as a substitute tendon which when implanted is freely slidable within the tissue.

A further object is to provide an improved structure for in vivo implantation as a substitute ligament which when implanted is secured in place by ingrowth of living tissue.

A still further object is to provide an improved structure for in vivo implantation as a substitute tension member which can be readily, simply and permanently secured to a body tension member to provide an extension for the body tension member.

Still another object is to provide an improved structure for in vivo implantation as a tension member having improved means for securing the ends in desired position without weakening the structure or the body structure to which it is attached.

Another object is to provide an improved method of making an implantable structure from a fabric and a film which assures the structural integrity of all of the fibers of the fabric.

BRIEF DESCRIPTION OF THE DRAWINGS

These and other objects and advantages of the present invention are hereinafter set forth and explained with reference to the drawings wherein:

FIG. 1 is a layout view of a form of the components of an elongate member which is to be used as a substitute tendon.

FIG. 2 is a plan view of a preferred form of structure to be implanted as a substitute tendon.

FIG. 3 is a schematic sectional view of the structure taken along line 3—3 in FIG. 2.

FIG. 4 is a schematic sectional view of the structure taken along line 4—4 in FIG. 2.

FIG. 5 is a sectional view of one form of attachment of the structure of FIG. 2 to a human tendon.

FIG. 6 is a plan view of a modified form of substitute tendon structure.

FIG. 7 is a schematic sectional view of the structure taken along line 7—7 in FIG. 6.

FIG. 8 is a sectional view of another form of attachment of the modified structure of FIG. 6 to a human tendon.

FIG. 12 is a schematic elevation view of a knee joint illustrating one form of installation of the substitute collateral ligament of the present invention.

FIG. 13 is a partial sectional view showing one form of attachment of substitute tension element to bone.

FIG. 15 is another schematic elevation view of a knee joint illustrating a modified form of installation of the substitute collateral ligament of the present invention shown in FIG. 14.

FIG. 16 is a detailed sectional view illustrating the securing of an elongate tension member to a tendon or ligament.

FIG. 17 is a plan view of a structure suitable for implantation as a patch with portions thereof broken away to illustrate the layers of the structure and with the upper right hand corner showing a modified form of the structure having a porous film.

FIG. 18 is a schematic sectional view of the structure shown in FIG. 17 taken along line 18—18.

DESCRIPTION OF THE PREFERRED EMBODIMENTS

Figure 9:
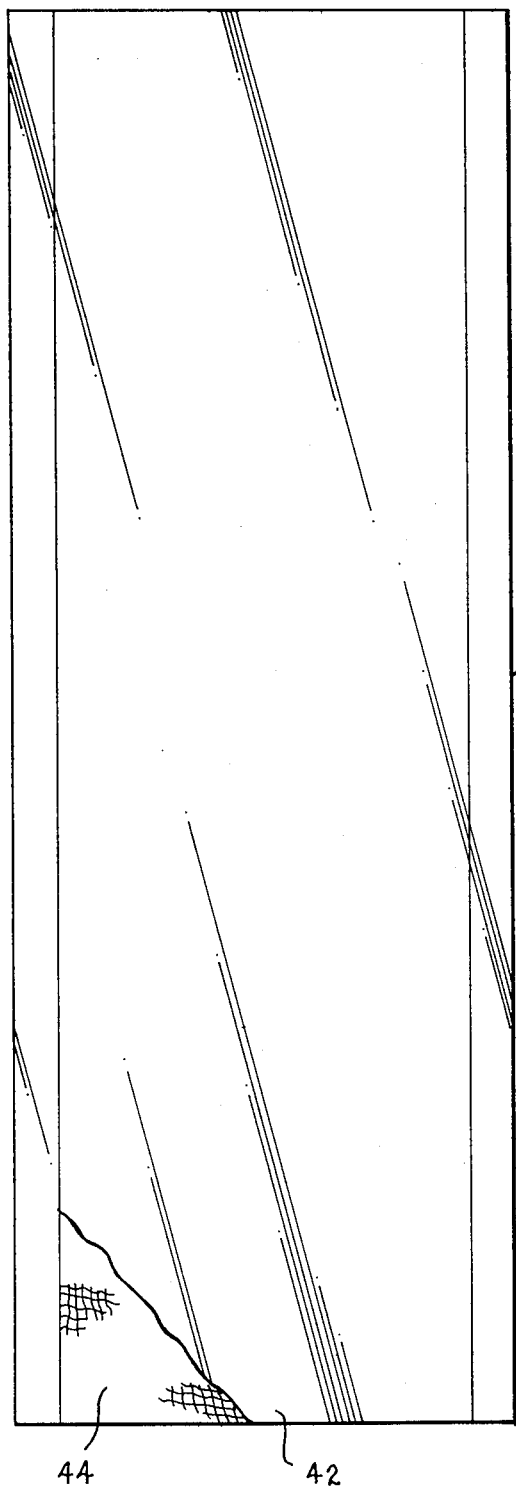
FIG. 9 is a layout view of a form of the components of an elongate member which is to be used as a substitute collateral or cruciate or combined collateral-cruciate ligament.

The structure of the present invention for in vivo implantation is composed of components which are biocompatible. The components include an elongate member which is composed of a fabric having a film heat bonded therein and a porous material which is associated with the elongate member at least near one end, said porous material being of a type which promotes the ingrowth of living tissue into its pores. An example of the preferred form of such porous material is the growth promoting material which is a fibrous porous structure having a critical surface tension of the fibers above 25 dynes per centimeter on a scale extending from 20 to 80 dynes per centimeter as disclosed in my copending application Ser. No. 145,497, filed May 20, 1971 (now abandoned) and its continuation application Ser. No. 416,641, filed Nov. 16, 1973 (now abandoned) which applications are incorporated herein by reference. Another example of a porous material which is suitable is a velour material of a polyester fiber such as the product sold by DuPont under the mark Dacron. The means for retaining the porous material with respect to the elongate member is hereinafter more fully described.

The elongate element is such that it has substantially no irreversible elongation or tension set in its axial direction and a predictable reversible elongation in its axial direction over the usual physiological stress range and has a degree of flexibility which may be preselected by the particular design of such element.

Also with respect to the structure of the present invention which is to be used as a substitute tendon a substantial portion of the exterior of the elongate element is of a material which resists tissue attachment when implanted.

With respect to the structure of the present invention which is to be used as a substitute ligament substantially all of the exterior of the elongate member is covered by the porous tissue growth promoting material.

In FIG. 1, the layout of the elongate member 10 which is to be used as a substitute tendon is shown to have a fabric 12 extending over its entire length. The central portion of fabric 12 is overlaid with the polymer film 14. The short portions 16 of the fabric 12 outside the film 14 are free of film and the short portions 18 outside the portions 16 are overlaid with film 20. The ends 22 of fabric 12 are free of film.

The elongate member 10 is formed from the materials as shown in FIG. 1 into the member 10 as shown in FIG. 2. Preferably the films 14 and 20 are heat bonded to the fabric 12 in the flat form shown in FIG. 1. The lamination is prepared by sandwiching the layers of polymer film and fabric. It is suggested that the sandwich may be surrounded by an aluminum foil. The sandwich is then placed in a heated press wherein responsive to heat and pressure the polymer film melts and flows into the interstices of the fabric. This develops an intimate and tough lamination of the polymer film and fabric.

In the preferred form of the invention a marquisette or "Leno-weave" fabric of polyamide (nylon) material such as the polyaramide, a polyamide originating from an aromatic amine monomer sold by DuPont Company under the mark "Nomex" is used. Such fabric is available from Stern & Stern, Inc. of Hornell, New York as fabric type HT-63-30. Other fabrics suitable for the invention are polytetrafluorethylene fabric and polyester fabric. In such fabric the fibers extending in one direction (warp) are disposed in twisted pairs such that the fibers extending in the perpendicular direction (fill) pass through the twisted pairs. With such fabric the warp direction is used parallel to the stress axis of the prosthesis or substitute tension member. With this fabric, the fibers in the stressed direction are prevented from slipping relative to the polymer matrix by the locking action of the fill fibers. The polymer film is preferable a perfluorocarbon such as is sold by DuPont Company under the mark "Teflon FEP". This film may be selected from the group consisting of a perfluorocarbon, a perfluoro ether fluorocarbon, a high molecular weight polyethylene and a hydrohalocarbon. Such material provides the prevention of attachment of tissue and engenders the formation of a tissue tunnel analogous to the natural peritendenous sheath. With these preferred materials, the initial pressing is accomplished with a suitable press temperature (platen surface temperature) of at least 550° F. and a pressure in the range from 10 psi to 200 psi and the time in the press may vary from 30 seconds to 5 minutes.

The lamination is removed from the press and quenched with distilled water. The particular dimensions of the elongate member at this stage are such as would provide the desired dimensions after subsequent processing for the particular implant application.

The quenched lamination is then folded lengthwise as shown in FIG. 3 (3 to 6 times for a tendon prosthesis and 5 to 20 times for a ligament prosthesis). The folded lamination is then placed within a heated press (550° F. to 600° F.) and molded at a pressure in the range from 40 psi to 250 psi for a period from 30 seconds to 10 minutes. The molded structure is cooled by water quenching to maximize flexibility and toughness.

The porous ingrowth material 24 is preset in the portions 16 from which the polymer film is excluded and is thereby contained at a position as shown in FIGS. 2 and 4 by the folding of the elongate member. The material 24 prevents distortion of the fabric and thus prevents fabric pore closure which normally results from tension. This structure is particularly advantageous in the securing of the end of the structure to a tendon 26 as shown in FIG. 5. As shown in such view the end of tendon 26 is pierced and the end of the structure is pulled through the pierced hole 27. The structure end is folded over with the porous ingrowth material 24 through such hole and the outer bonded end of the structure is secured to the structure as shown. This structure is suitably sutured as at 28 to secure the porous material 24 on both sides of the end of tendon 26. With the ingrowth of tissue through the fabric 12 at 16 which is maintained open by the porous material 24 and into material 24 a materially reinforced connection is provided to the tendon 26. The sutures may be provided by removing the transverse threads from the fabric of the unbonded ends of the member 10 as shown in FIG. 2.

An alternate structure 10a for the end of the structure is shown in FIG. 6 wherein the material 24a is suitably bonded to both sides of the outermost bonded portions of the elongate member. The material for this bonding should be suitable both to the film 14 and the material 24a. A bonding material of perfluorocarbon such as sold by DuPont Company as "Teflon FEP" has been found suitable for such bonding with the above mentioned preferred materials. This bonding is then accomplished by heat and may be done in a press as a separate operation or as a pair of the forming of the elongate structure.

This modified end of the substitute tendon structure is used to connect to a tendon as shown in FIG. 8. The unbonded portions 16a of the elongate member 10a are prepared by removing the transverse threads of the fabric 12a. With the fabric portion 16a opened the tendon 30 is pulled through the opening, doubled back on the porous material 24a and sutured as shown.

Another form of attachment of the substitute tendon structure to a human tendon is shown in FIG. 16 wherein the tendon 30b is split axially and the end of a substitute tendon 10b with the growth material 24b thereon (similar to tendon 10a shown in FIGS. 6 and 8) is placed between the ends of tendon 30b and is suitable sutured in such position as shown.

The substitute ligament structures of the present invention are of much larger size than the substitute tendon structure and have in their final form substantially their entire outer surface covered with the porous growth promoting material as previously mentioned.

Figure 10:
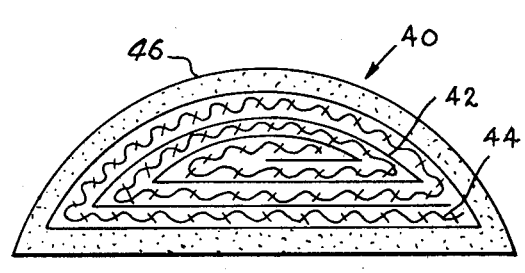
FIG. 10 is a schematic transverse sectional view of the preferred form of substitute cruciate ligament.

The layout illustrated in FIG. 9 is of a substitute collateral cruciate or combined collateral cruciate ligament. As with the previously described substitute tendon structures, the layout shows only the elongate member 40. The member 40 includes the film 42 and the fabric 44 with the film 42 extending beyond the edges of the fabric 44. As may be seen the entire length of this elongate structure 40 is uniform in construction in the fabric 44 being embedded in polymer matrix film 42 and with a suitable porous growth promoting material 46 surrounding the formed element 40 as is shown in FIG. 10.

The elongate element is folded and formed in a heated press in exactly the same manner previously described with respect to the tendon. Also, the complete structure is covered with the porous growth promoting material which is bonded thereto by a suitable bonding material as previously explained.

Since it is contemplated that many of the substitute tension elements of the present invention may be secured by stapling it is preferred that the elements be prepared to have suitable placed apertures along its length. This is done by passing probes heated to a temperature between 500° to 700° F. These apertures are spaced to accommodate the tines of a surgical staple. The provision of these apertures allows a staple to be placed without mechanical disruption of the fibers within the element. The use of the heated probes allows melting or sufficient softening of the matrix for the probes to enter and a gentle movement of the fibers by the probes allows the apertures to be developed without mechanical rupture of the fibers whereby the longitudinal tensile strength of the element is preserved. When formed as shown in FIG. 10 the structure 40 is preferred to have the shape of a segment of a circle.

Figure 11:
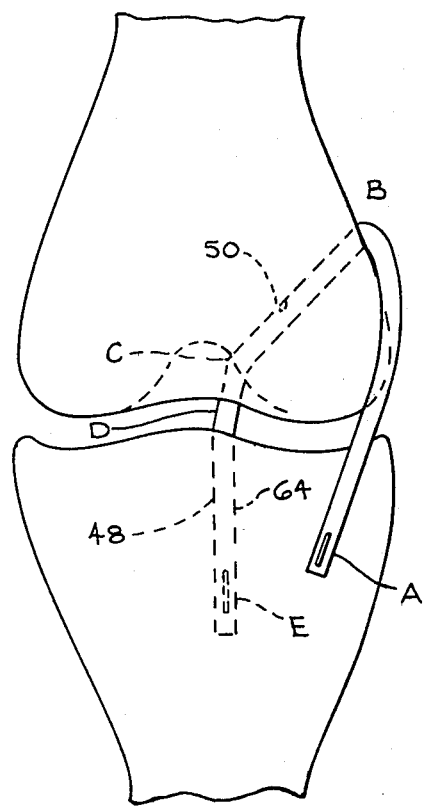
FIG. 11 is a schematic elevation view of a knee joint illustrating the implantation of the substitute combined collateral-cruciate ligament of the present invention shown in FIG. 9.

The tension structure 40 may be used as a substitute combined cruciate collateral ligament as shown in FIG. 11. The structure 40 passes from a fixation point E below the flare of the proximal tibia through a tunnel 48 emerging at D within the joint space and entering the femur at point C, passing through a tunnel 50 in the femur emerging at point B. If desired the surgeon may secure the end of the structure 40 to the femur and cut off the excess length and in such case the structure functions only as a cruciate ligament. If desired however, the structure may be carried back down over the joint line on the lateral or medial side of the joint for fixation to the tibia at point A. In this way a single structure 40 may serve not only a cruciate reconstruction role but also a collateral ligament reconstruction role.

The tension element structure 40 may also be used as a substitute collateral ligament as shown in FIG. 12. The structure 40 is suitably secured to the tibia as by stapling, extends across the joint and through the tunnel 52 in the femur and is secured on the opposite side of the femur by stapling as shown in dashed lines at 54.

The ends of the substitute tension elements may be secured to a bone as shown in FIG. 13 by developing a tunnel 56 in the bone, passing the structure 40 therethrough and folding it back onto itself for the addition of the sutures 58 to secure the element 40 in its desired position.

In some applications of the improved tension element of the present invention, the structure may function as a tendon ligament combination. For example, with a humeral head prosthesis one end of the tension structure is secured to the prosthetic humeral head and the other end secured to the appropriate tissue structures utilizing the ingrowth materials such as previously discussed with respect to substitute tendons.

Figure 14:
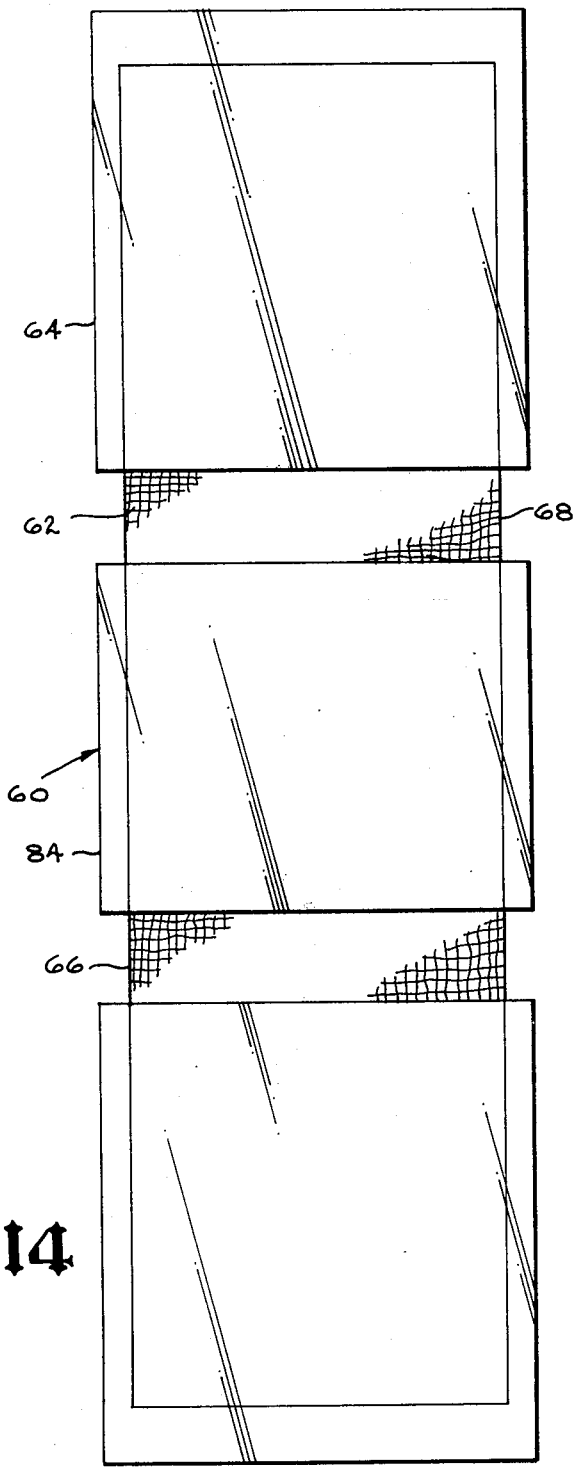
FIG. 14 is a layout view of a modified form of elongate member to be used as a collateral ligament.

The structure shown in FIG. 14 is a layout of a modified form of substitute collateral ligament. The structure 60 includes the fabric 62 and the film 64. The layout form the structure has two open fabric portions 66 and 68 with no film thereon. The structure 60 is folded to have the collateral ligament flat form and is designed to be used as shown in FIG. 15. The structure 60 extends through a tunnel 70 in the upper portion of the tibia and both ends are taken across the joint space and suitable secured as by stapling to the lower portion of the femur. The open spaces 66 and 68 allow freedom of the structure leaving the tunnel 70 to be sufficiently flexible to extend to the femur as shown. Such flexibility is only for each in implanting the structure. It should be noted that the open spaces which provide such increased flexibility should not be positioned so that they might flex when the knee is flexed. Such flexing could result in premature failure of the structure resulting from concentration of the flexing in the point of greater flexibility.

In the tension element of the present invention and particularly in the forms adapted to be used as a substitute ligaments it is considered desireable to include a small suture wire in the layout of the tension structures so that it would be secured in the completed structure to serve as an X-ray marker to assist in locating the position of the implant.

The combination of the fabric and film of the present invention in its layout bonded form may be used as a layer strengthening patch. Such structure may be used as a patch for soft tissue such as a hernia patch and for hard tissue or bone such as a skull patch. The form of patch structure 72 shown in FIG. 17 includes the fabric 74, the film 76 and the growth promoting material 78 which is bonded to one side or to both sides of the patch structure 72 as shown in FIG. 18. A patch with growth material on only one side would be suitable as an intraperitoneal patch. If desired the film may be solid completely across the patch as shown in the lower left hand portion of FIG. 17 to prevent permeation therethrough or may be uniformly porous as shown in the upper right hand corner of FIG. 17 to exhibit substantial permeation to body fluid.

It should be noted with the implantable structure of the present invention that if additional stiffness is needed then thicker or additional layers of film should be used. To increase the strength of the structure the amount of fabric should be increased or a stronger fabric used.

From the foregoing it can be seen that the present invention provides an improved structure for in vivo implantation as a substitute tension member, which structure may be used as a tendon or tendon extension as a ligament or as a combined tendon ligament structure and further improved attachment structures are provided for securing to tendons and also to bones. Further the present invention provides an improved implantable patch structure which may be made permeable or non-permeable to body fluids as desired. The improved method of the present invention assures that the implantable structure has complete integrity of its components.

What is claimed is:

1. A structure suitable for in vivo implantation comprising a biocompatible fabric, a biocompatible film being heat formed into at least a portion of said fabric to set the fabric, said fabric being heat stable at the heat forming temperature of said film, said fabric having a weave in which fibers extending in one direction are disposed in twisted pairs whereby when said film is heat formed into at least a portion of said fabric said structure has substantially no permanent yield in one direction responsive to physiological stresses.

2. A structure according to claim 1 wherein,
said structure being formed into an elongate element,
said elongate element having an open portion near one end and growth promoting material bonded to the end beyond the open portion whereby a body tension element may be passed through the open portion and secured to be in contact with said growth promoting material at the outer extremity of said open portion.

3. A structure according to claim 1 wherein
said fabric is selected from the group consisting of a polyamide fabric, a polytetrafluoroethylene fabric and a polyester fabric, and
said film is selected from the group consisting of a perfluorocarbon, a perfluoro ether fluorocarbon, a high molecular weight polyethylene and hydrohalocarbon.

4. A structure according to claim 1, including a biocompatible porous material which promotes ingrowth of living tissue within its pores secured to said structure.

5. A structure according to claim 3, wherein portions along the length of said structure is free of film.

6. A structure according to claim 4, wherein said porous material is a polyester fiber velour material.

7. A structure according to claim 4, wherein
said porous material is a fibrous porous material having a critical surface tension of the fibers above 35 dynes per centimeter.

8. A structure according to claim 4, wherein
said porous material is positioned within a section of film free fabric near the end of said structure.

9. A structure according to claim 4, wherein
said porous material is bonded to the exterior of said structure near the ends.

10. A structure according to claim 4, wherein
said film and said fabric are folded lengthwise and formed into an elongate member.

11. A structure according to claim 10, wherein
said porous material completely surrounds portions of the exterior of the elongate member.

12. A structure according to claim 10, wherein
said elongate member has apertures therethrough which do not sever nay of the fabric fibers.

13. A structure according to claim 1, including
a biocompatible porous material having the characteristic of promoting ingrowth of living tissue and being bonded to at least a portion of one side of said film and fabric structure.

14. A structure according to claim 13, wherein
said porous material being contained within a porous portion of said structure.

15. A structure according to claim 13, wherein
said porous material is bonded to said structure and covers substantially all of the exterior surface of said structure.

16. A structure according to claim 15, wherein
said structure is in the shape of an elongate element having a transverse sectional shape of a circle segment.

17. A structure according to claim 16, wherein
portions of said elongate element are relatively more flexible than other portions.

18. A structure according to claim 16, wherein
a portion of said elongate element spaced a short distance from one end includes only axially extending portions of a fabric forming a part of the remaining portion of said elongate element.

19. A structure according to claim 16, wherein
said elongate element is of a material which resists tissue growth attachment.

20. A structure suitable for in vivo implantation, consisting essentially of
a biocompatible fabric,
a biocompatible film,
said fabric being stable at the melting temperature of said film,
said film being heat formed into said fabric, and
a porous growth promoting material being bonded directly to the combined film and fabric structure.

21. A structure according to claim 20, wherein
said growth promoting material is bonded to both sides of said combined film and fabric structure.

22. A structure according to claim 21, wherein
said film completely covers said fabric whereby the structure exhibits substantially no permeation to body fluids.

23. A structure according to claim 21, wherein
said film is uniformly porous over said fabric whereby the structure exhibits substantial permeation to body fluids.

* * * * *

UNITED STATES PATENT OFFICE
CERTIFICATE OF CORRECTION

Patent No. 4,127,902            Dated December 5, 1978

Inventor(s)     Charles A. Homsy

It is certified that error appears in the above-identified patent and that said Letters Patent are hereby corrected as shown below:

Column 1, line 17,   "damage" should read "damaged"

Column 7, line 43,   "nay" should read "any"

Signed and Sealed this

First Day of May 1979

[SEAL]

Attest:

RUTH C. MASON  
Attesting Officer

DONALD W. BANNER  
Commissioner of Patents and Trademarks